United States Patent [19]
Klein

[11] Patent Number: 5,984,674
[45] Date of Patent: *Nov. 16, 1999

[54] ORTHODONTIC O-RING LIGATOR WAND CHARGER

[76] Inventor: Paul E. Klein, 928 Lake Shore Rd., Lake Oswego, Oreg. 97034

[*] Notice: This patent issued on a continued prosecution application filed under 37 CFR 1.53(d), and is subject to the twenty year patent term provisions of 35 U.S.C. 154(a)(2).

[21] Appl. No.: 08/704,414

[22] Filed: Aug. 21, 1996

[51] Int. Cl.[6] ................................................. A61C 7/00
[52] U.S. Cl. ................................. 433/2; 433/18; 206/63.5
[58] Field of Search ........................... 433/2, 3, 11, 18; 606/140, 148; 206/63.3, 63.5, 339, 805

[56] References Cited

U.S. PATENT DOCUMENTS

| | | | |
|---|---|---|---|
| 3,713,533 | 1/1973 | Reimels | 206/339 |
| 4,026,021 | 5/1977 | Kesling | 433/2 |
| 4,330,271 | 5/1982 | Anderson | 433/3 |
| 4,412,820 | 11/1983 | Brummond et al. | 433/18 |
| 4,901,847 | 2/1990 | Kesling | 433/2 |
| 4,946,385 | 8/1990 | Eckert et al. | 433/18 |
| 4,946,386 | 8/1990 | Kidd et al. | 433/18 |
| 5,013,238 | 5/1991 | Sterrett et al. | 433/18 |
| 5,054,647 | 10/1991 | Yawata | 433/3 |
| 5,326,260 | 7/1994 | Klein et al. | 433/11 |

FOREIGN PATENT DOCUMENTS

| | | | |
|---|---|---|---|
| 316106 | 5/1989 | European Pat. Off. | 433/2 |

*Primary Examiner*—Ralph A. Lewis
*Attorney, Agent, or Firm*—Kolisch Hartwell Dickinson McCormack & Heuser

[57] ABSTRACT

A charger/dispenser for orthodontic O-ring ligator structure including a body, friction retaining structure formed in the body for retaining, frictionally and releasably such a ligator structure in a condition with each ligator in the ligator structure having a substantially fully exposed annular face, and hemostat-jaw guide structure formed in the body effective to guide the gripping beaks in the jaw of a hemostat into a limit-defined removing position relative to such a ligator wherein a jaw can fully grip the ligator without occluding the open center therein.

16 Claims, 3 Drawing Sheets

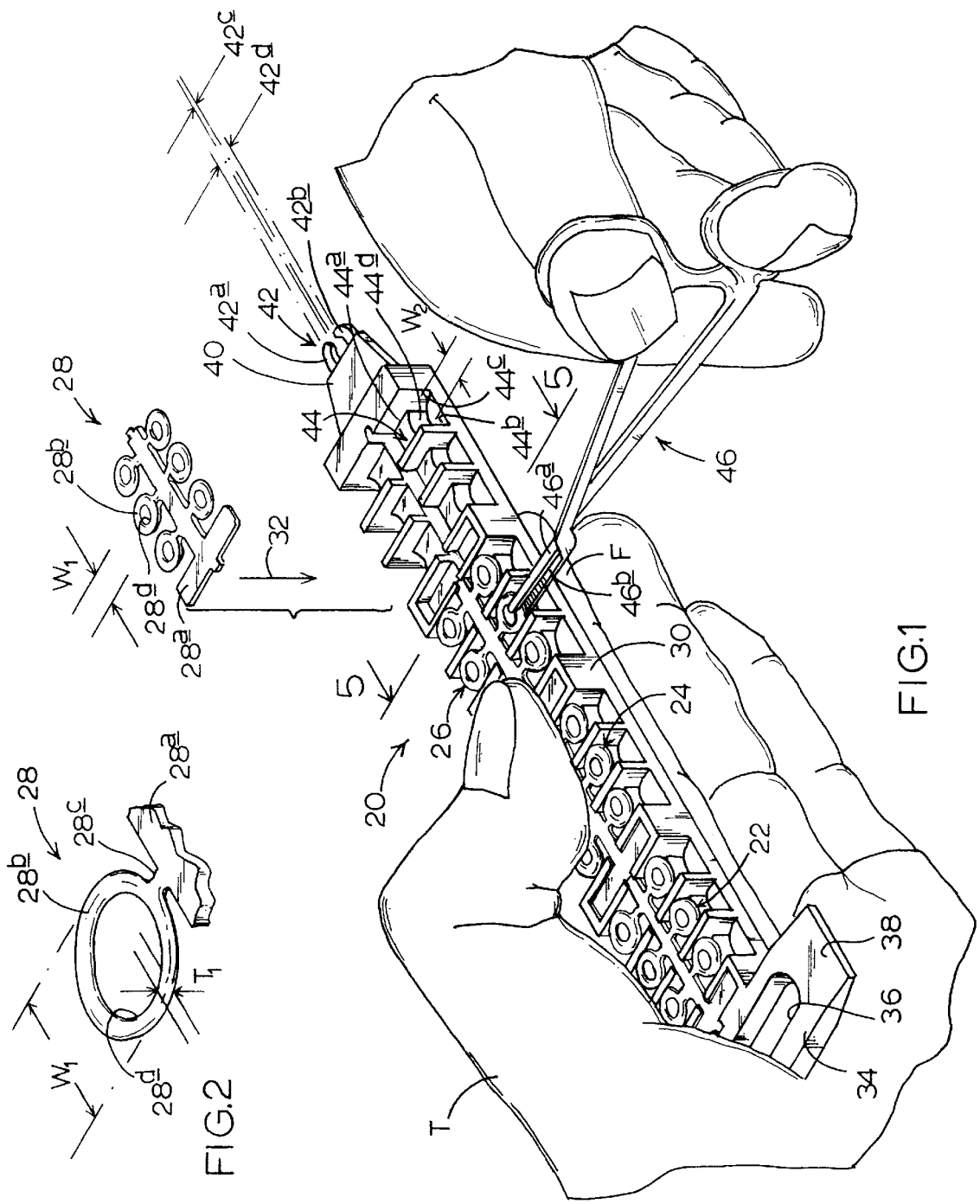

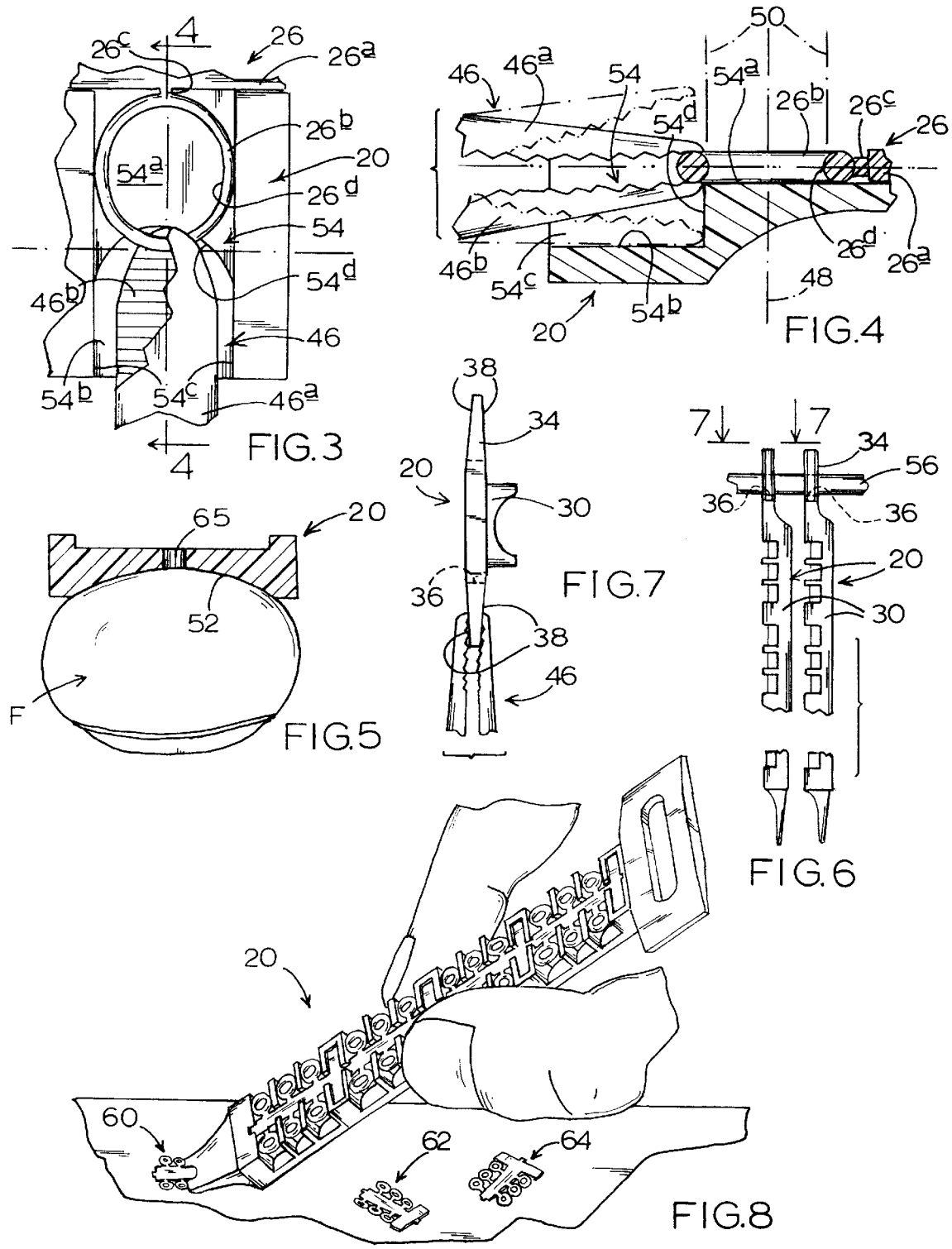

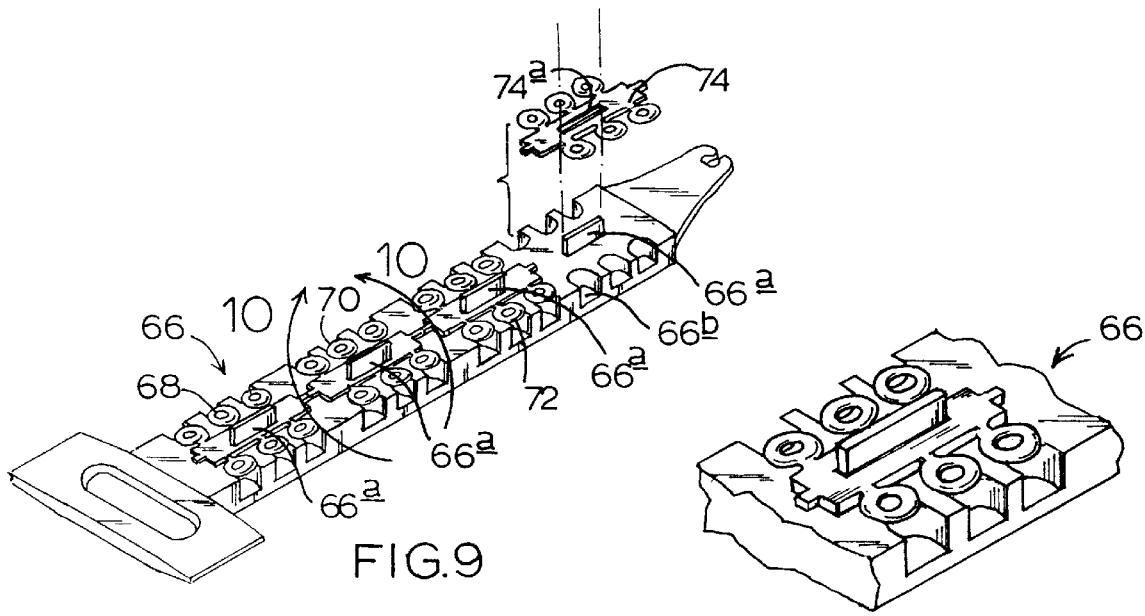
FIG.9
FIG.10
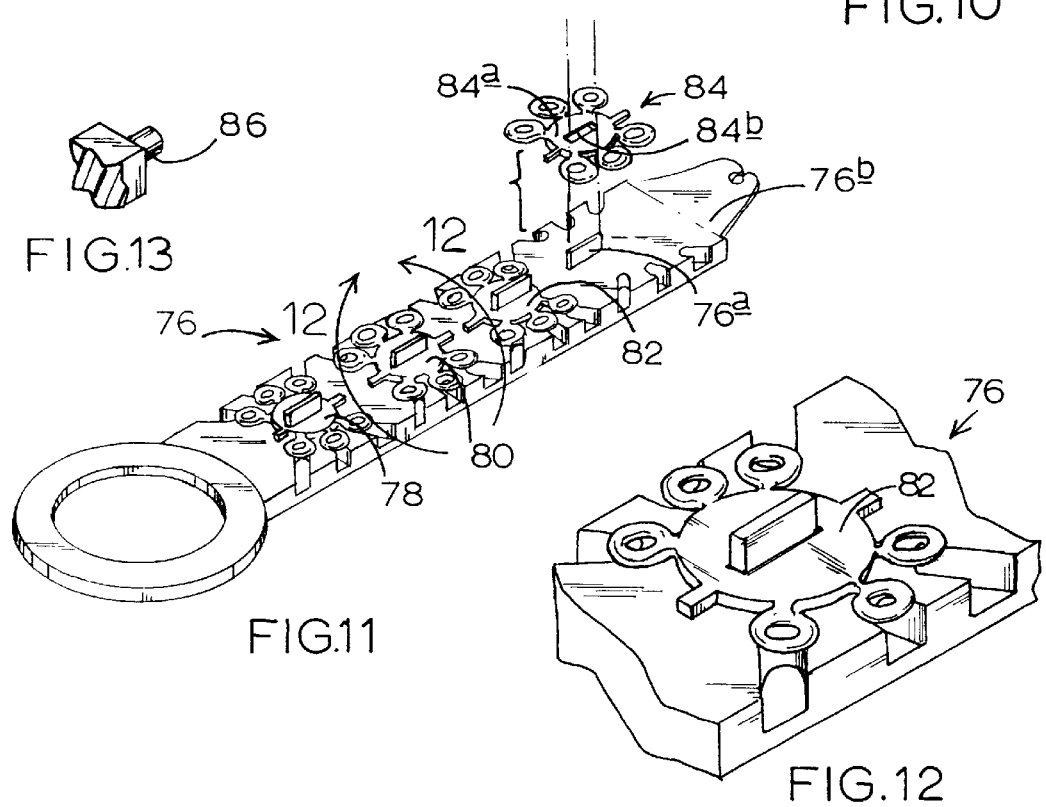
FIG.11
FIG.13
FIG.12

ORTHODONTIC O-RING LIGATOR WAND CHARGER

BACKGROUND AND SUMMARY OF THE INVENTION

This invention relates to the field of orthodontics, and in particular to what I refer to as a charger/dispenser for facilitating the handling of small, unitary collections of sprue-borne, orthodontic, elastomeric O-ring ligators.

Orthodontic O-ring-like elastomeric ligators have been around now for roughly twenty years, and during that time period this field has seen many advances which relate to the ways in which such ligators are carried and/or presented for handling. For example, various dispensing and handling techniques, apparatuses and arrangements are illustrated in U.S. Pat. Nos. 3,903,601 to Anderson et al. (ligators formed in an elongate chain), 4,038,753 to Klein (ligators carried on the sides of an elongate sprue-like member), 4,330,271 to Anderson (disclosure similar to that found in the '753 patent), 5,016,756 to Klein et al. (ligators formed on the sides of an elongate wand), 5,221,033 to Klein et al. (ligators formed in an elongate chain), and 5,326,260 to Klein et al. (small grouping of ligators formed as a "six-pack" carried on opposite sides of a T-shaped, central, sprue-like wand).

The present invention, as illustrated herein, pertains, generally, to the handling of six-pack-like groupings of sprue-borne ligators very much like what is shown in the above-mentioned '260 patent. While the handling of six-pack-like ligator groupings is chosen for illustration in this disclosure, the invention is not confined, of course, and as will become apparent, to the handling only of such groupings. Nevertheless, orthodontists have found that a very convenient grouping of ligators is one that contains about six to a group, and thus it is in relation to handling this convenience-recognized grouping that the features of the present invention are described and illustrated herein.

Regarding the handling of such ligators, a recent fad-like phenomenon which principally focuses on aesthetics rather than on performance is that elastomeric O-rings are being requested, and accordingly manufactured, in a wide variety of brilliant, almost luminescent colors which cause them to be highly visible when in place on a patient. Oddly enough, while, in early years, patients wearing orthodontic apparatus were somewhat embarrassed by how these things looked, it is today quite the rage, particularly among very young patients, to put on, so-to-speak, a rainbow display of colors. Thus, it would be typical for a patient to ask an orthodontist to install not just ligators of a single color, but ligators of many many colors.

Accordingly, multiple color choices in elastomeric ligators have injected a tremendous boost to orthodontics, in that an element of visual fun has been introduced. The concept has arisen that these appliances are or can be viewed not as unsightly things, but rather as something more in the category of custom jewelry.

However, keeping track of such small groups of multicolored ligators is a bit of a problem, and although it is certainly amusing for the patient to be able to specify and be able to display multiple colors of ligators, for the orthodontist, keeping track of these and handling and manipulating them is quite time consuming, and can be confusing. Additionally, it takes a fairly high degree of visual and tactile coordination, for example, to grasp just the "tire portion" of tiny O-ring ligators with a hemostat, and this can present the issues (1) that if you get too much, you tend to block the open portion of a ligator, and (2) if you get too little, it might tear or come loose from a hemostat's grip.

The present invention deals with all of these matters in a highly satisfying and simple manner.

According to a preferred embodiment of the invention, what is provided thereby is a rigid, elongate, bar-like body which has been formed in such a fashion that it can frictionally and releasably receive and grip a collection (four in the preferred embodiment illustrated and described herein) of T-bar-like, sprue-borne six-packs of ligators, each of which may be a different color. As will become apparent from the description which follows below, gripping occurs frictionally between surface structure which forms part of the bar-like body and surface structure in the central sprue which holds ligators. This device, which preferably is formed of a suitable molded plastic material that can be conventionally sterilized for repeated use, is formed with specially sized, spaced and shaped void spaces, or recesses, which act to guide the jaw of a hemostat so that the beaks in that jaw properly and fully grip the tire of each ligator without occluding the central open space therein. The device proposed by the invention thus conveniently organizes a collection of ligators in a manner that promotes easy handling, manipulation and dispensing by an orthodontist.

At one end of the device, as proposed in accordance with a preferred embodiment thereof, there is provided a double-tined, fork-like protrusion (plucking element) which can be used to pick up, for example, a loose sprue-borne ligator six-pack from a work surface or from a box containing a plurality of such things.

The device of the invention further includes a handle through which extends an opening that allows multiple like devices to be hung, for example, on a supporting rail. The sides of the outer ends of these handles are formed, as can be seen when viewed from the ends, with a very slight, laterally outwardly converging taper that just about exactly matches the angle formed in the open jaw of a hemostat when such is opened the amount that would be required to use the hemostat to grip the device. Thus, an orthodontist, without having physically to touch such a device in the process of freeing one for use from a hanging collection of multiple ones of these devices, can do so with a sterilized hemostat which leaves intact the sterility of neighboring devices in a hanging collection.

Various other features and advantages that are offered by the present invention will become more fully apparent as the description which now follows is read in conjunction with the accompanying drawings.

BRIEF DESCRIPTION OF THE DRAWINGS

FIG. 1 is a larger-than-life-scale perspective view illustrating a preferred embodiment of the invention in use with four T-bar-like, sprue-borne, elastomeric ligator six-packs of the type mentioned above, with one of these packs being shown spaced above and not gripped by the device, and with a hemostat being shown accessing for use one of the carried ligators.

FIG. 2 is a view on a larger scale than that used in FIG. 1, illustrating, fragmentarily and in free space, one ligator and a portion of a connected sprue of the type shown carried in FIG. 1.

FIG. 3 is an enlarged and fragmentary view, on about the same scale employed in FIG. 2, illustrating in detail, and from a plan point of view, the beaks in the jaw of the hemostat illustrated in FIG. 1.

FIG. 4, which is also on about the same scale as that used in FIGS. 2 and 3, is a fragmentary sectional view taken generally along the line 4—4 in FIG. 3.

FIG. 5 is a view on approximately the same scale employed in FIG. 1, taken generally along the line 5—5 in FIG. 1.

FIG. 6, which is on a smaller scale than that characterizing FIG. 1, illustrates fragmentarily a pair of devices as illustrated in FIG. 1 carried (hanging) on and from a supporting rail.

FIG. 7, which is on a larger scale than that employed in FIG. 6, is a view taken generally along the line 7—7 in FIG. 6 illustrating a hemostat-gripping taper which is formed in the handles of devices made in accordance with the preferred embodiment of the invention.

FIG. 8, which is on about the same scale of that used in FIG. 6, illustrates the use of a two-tined fork at one end of the invention being employed to pick up an otherwise free and not yet loaded and carried sprue-borne six-pack of ligators.

FIG. 9, which is on a slightly smaller scale than that used in FIG. 1, illustrates a modified form of the invention employed to carry a modified form of ligator six-pack.

FIG. 10 is an enlarged, fragmentary detail of the area embraced in FIG. 9 by curved arrows 10—10.

FIG. 11, which is on about the same scale as that seen in FIG. 9, illustrates yet another modified form of the invention designed to carry and dispense yet another modified form of ligator six-pack.

FIG. 12 is an enlarged fragmentary detail of that area in FIG. 11 which is embraced by curved arrows 12—12.

FIG. 13 is a fragmentary detail taken as if from the right ends of the charger/dispenser units pictured in FIGS. 9 and 11, illustrating a modified form of plucking element.

DETAILED DESCRIPTION OF THE INVENTION

Turning attention now to FIGS. 1 and 2 in the drawings, indicated generally at 20 in FIG. 1 is an elongate charger/dispenser which is constructed in accordance with a preferred embodiment of the present invention for carrying and facilitating the use and manipulation of a plurality (four in the case now being described) of T-bar-like, sprue-borne ligator six-packs, such as the four shown at 22, 24, 26, 28. Charger/dispenser 20 is preferably formed of a suitable molded plastic material that is capable withstanding conventional sterilizing procedures, and herein, is formed of the material known as Ultem® which is a product of General Electric Company. The body 30 in the charger/dispenser is designed with the apparent upper surface topography between its ends, which topography is clearly illustrated in FIG. 1. This topography is designed to receive, frictionally and grippingly, four six-packs of O-ring ligators like those just mentioned above. Packs 22, 24, 26 are shown in conditions charged and held in the charger/dispenser, and pack 28 is shown in an elevated condition ready to be stored in the charger/dispenser by pressing it downwardly in the direction of arrow 32. In the embodiment now being described, gripping of packs 22, 24, 26 occurs principally by frictional engagement and pinching of the elongate central sprues (mentioned more fully below) in each of the packs, which sprues carry the six to-be-dispensed O-ring ligators. The near end of the body in FIG. 1 includes a generally rectangular, thin handle 34 which includes a central opening 36, and on opposite sides, a very gently tapered profile, such as that indicated generally at 38. The far end of the body in FIG. 1 includes a projection 40 which terminates with a two-tined plucking fork 42 which is employed in a manner that will shortly be described.

Fork 42 includes laterally spaced tines 42a, 42b. The spacing between these tines defines, generally, a narrow entrance throat 42c, and a somewhat wider curvilinear pocket 42d.

Each of the O-ring six-pack ligator structures includes a T-bar-shaped sprue, such as sprue 28a, having a long central finger to the opposite sides of which are joined (three on each side) six, round-cross-section, O-ring, snap-detachable ligators, such as ligator 28b. A fragment of unit 28 is shown in FIG. 2, and here one can see that ligator 28b is joined to sprue 28a through a tiny elastomeric isthmus 28c. Sprue 28a is also referred to herein as a carrier. A certain story-telling and illustration license has been employed in relation to depiction in the figures of the ligator six-packs, in that the O-rings are shown somewhat out of proportion. More specifically, the O-ring ligators in "actual life" have thicker round cross-sections in relation to the diameter of the central openings, and if depicted in exact proportion, would appear to have relatively significantly smaller central openings.

As is illustrated in FIGS. 1 and 2, and in the particular situation now being discussed, each ligator has a cross-sectional thickness indicated in FIG. 2 at $T_1$, and an outer diameter indicated in FIGS. 1 and 2 at $W_1$. Each ligator, as is also evident from FIGS. 1 and 2, has a tire-like shape with a central opening, such as that shown at 28d.

A feature of the invention is that, with respect to each topographic area within what is the upper side of charger/dispenser 20 in FIG. 1 which is designed to receive a single six-pack of the type mentioned, there are upwardly facing recesses, such as unfilled recess 44, provided to receive each O-ring ligator. In charger/dispenser 20, and in specific relation to the particular size six-pack illustrated, these recesses have a width, indicated at $W_2$, which is just slightly smaller than previously mentioned width $W_1$. As a consequence, these recesses slightly compress the ligators and thus assist modestly in frictionally gripping them in place. This is the condition which is illustrated for six-packs 22, 24, 26 in FIG. 1. Accordingly, this recess structure, along with central gripping channel 20a is referred to also herein as friction retaining structure.

As can be seen for recess 44, what can be thought of as the base of the recess is stepped in a fashion including an upper level 44a and a lower level 44b. Upper level 44a is referred to as a ligator supporting surface. The lower portion of recess 44 which extends inwardly from the far end, near side of charger/dispenser 20 in FIG. 1 is referred to herein as a guide canal which opens both to the upper surface of the charger/dispenser and to the side thereof This guide canal is defined by a floor which has been referred to previously with reference character 44b, by a pair of side walls, such as side wall 44c, and by what is referred to herein as will be explained as a limit-defining curvilinear back wall 44d.

In FIG. 1, charger/dispenser 20 is illustrated being held between the left thumb and forefinger of an orthodontist, with the right hand of the orthodontist fragmentarily shown being illustrated holding a hemostat 46 in a position with its beaks 46a, 46b ready to grip, pluck and remove one of the ligators contained in six-pack 26. The orthodontist's left thumb, indicated in phantom lines at T, presses against the top of six-pack 26, and his or her forefinger, indicated at F, presses against the underside of the handle and extends along a portion of the underside of body 32 in a shallow, concave, curved, elongate recess which extends substantially along the entire length of the body, which recess is illustrated at 52 in FIG. 5 (second plate of drawings).

Addressing attention now to FIGS. 3, 4, and 5 along with FIGS. 1 and 2, FIGS. 3 and 4 illustrate the condition which exists adjacent the beaks in the jaw structure of hemostat 46 where it is positioned (as illustrated in FIG. 1) to grasp a ligator from six-pack 26 which is frictionally held in a recess 54 that is like previously described recess 44.

The construction of recess 54 is substantially identical to the construction of recess 44, and its constituents herein are labeled in a manner consistent with labeling of the like constituents in recess 44. Thus recess 54 includes an upper level 54*a*, a lower level 54*b*, a pair of side walls 54*c* which, in a curvilinear fashion, converge to blend with and to form a back wall 54*d*, the deep center of which defines the same kind of limit-defining back wall just mentioned above.

Parts in six-pack 26 are shown in FIGS. 3 and 4 with labeling that is similar to that employed for parts in previously discussed six-pack 28. Thus, one can see in six-pack 26 its central sprue 26*a* and a tire-like ligator 26*b* which is joined to the sprue through a tiny isthmus 26*c*. The central opening in ligator tire 26*b* is shown at 26*d*, and in FIG. 3, a slight compressing of tire 26*b* in recess 54 is evident. In FIG. 4 the central axis of opening 26*d* is indicated by dash-dot line 48, and the diameter of the opening, measured along a left-to-right line contained within the plane of FIG. 4, and with tire 26*b* in its illustrated, slightly compressed state, is indicated by the spacing between dash-dot lines 50 in FIG. 4.

Recalling the discussion given above relating to the construction of recess 54, one can observe how, when advancing the beaks in the jaw of hemostat 46 toward a position for grasping tire 26*b*, and with these beaks relatively widely spaced as illustrated in dash-dot lines in FIG. 4, the lower beak is neatly guided into the lower portion of the recess between the side walls and the curving back wall in a natural way to define a limit ingress position for the hemostat. In this position/condition, the tip of the lower beak is driven centrally against the curved back wall of that lower portion. The hemostat is then closed (as illustrated in solid lines in FIG. 4) to grip a laterally outwardly extending portion of ligator tire 26*b*, and one can observe from both FIGS. 3 and 4 that such gripping occurs in a manner whereby the jaw amply and fully grips the tire without in any way appreciably occluding opening 26*d*. The orthodontist, with tire 26*b* gripped, simply snap-pulls the tire away, with isthmus 26*c* breaking thus to release the ligator for use.

With attention now drawn to FIGS. 6 and 7, FIG. 6 illustrates a display/storage arrangement for plural charger/dispensers, and two of such dispensers, each bearing the same reference numeral 20, are illustrated fragmentarily in FIG. 6 in a condition hanging from an elongate rail 56. More specifically, these charger/dispensers are disposed with rail 56 extending through openings 36 in handles 34. The fact that handles 34, as clearly pictured in FIG. 6, have lateral dimensions about half those of the downwardly extending remaining portions of bodies 30, causes there to be a spacing gap between each adjacent handle even under circumstances where adjacent charger/dispensers abut one another.

Facing the viewer in FIG. 6 in each of the two handles displayed therein are previously mentioned tapered profiles 38, a pair of which, formed on the left hand charger/dispenser in FIG. 6, are pictured clearly on a larger scale in FIG. 7. These profiles have tapers which just about exactly match the angle that will exist at the outer end of the jaw of a hemostat, like hemostat 46, when this jaw is substantially in contact with such a tapered portion. Thus, the charger/dispenser of the invention allows easy hemostat gripping and removing as an individual of a charger/dispenser from a storage system like that illustrated in FIG. 6. In particular, it allows handling and removal of a charger/dispenser without direct human contact, and thus in a condition which minimizes the likelihood of contaminating a not-yet-to-be-removed charger/dispenser.

FIG. 8 in the drawings illustrates another interesting and very useful feature of charger/dispenser 26. Here there are illustrated on a fragmentarily shown support surface 38 plural ligator six-packs 60, 62, 64 which are in what might be thought of as loose, free-standing conditions. These packs, for example, might be contained within a box in which they are supplied to an orthodontist's office.

FIG. 8 specifically illustrates use of fork 42 in charger/dispenser 20 to grip and pick up such a pack, without direct human touch, and in FIG. 8, a charger/dispenser bearing the same reference numeral 20 is illustrated being manipulated by the right hand of an orthodontist to pick up six-pack 60.

The final feature found in the embodiment of the invention now being described is the presence of four through-body holes, such as hole 65 pictured in FIG. 5, located centrally adjacent the opposite ends of the recesses which receive the ligator six-packs, which holes permit the poking through of a skinny tool of any sort for quick removing of a "spent" ligator six-pack from the charger/dispenser. Each of these holes is referred to herein as a ligator-structure-ejection passage.

Switching attention now to FIGS. 9 and 10, here there is shown generally at 66 a charger/dispenser which is constructed in accordance with a modified form of the invention. Dispenser 66 is designed to receive a charge of somewhat modified six-packs of ligators, such as the four shown at 68, 70, 72, 74 in FIG. 9. Packs 68, 70, 72 are shown each in a received and fricitonally contained condition, and six-pack 74 is shown spaced from the charger/dispenser in a condition ready to be stored thereon.

The six-packs illustrated in FIG. 9 contain elongate rectangular openings, such as opening 74*a* in six-pack 74. Accordingly, charger/dispenser 66 is formed with elongate, upright, rectilinear posts 66*a* which are adapted to extend frictionally through openings, such as opening 74*a*, thus acting as the principal structure which retains a ligator six-pack frictionally in place. Adjacent each post are laterally and upwardly openly facing recesses, such as those shown at 66*b* which include lower portions with side walls merging with a curved back wall that define hemostat guide structure very much like that which was described in conjunction with charger/dispenser 20.

In other respects, charger/dispenser 66 is very much like charger/dispenser 20, and this similarity should be plain to one looking at the relevant drawings. A hemostat which is directed to grip, pluck, and remove a ligator is ingression limited as described before so that it can entirely grip a tire in a six-pack without appreciably occluding the addressed ligator's open center.

FIGS. 11 and 12, which are similar to the points of view illustrated in FIGS. 9 and 10, respectively, illustrate yet another form of charger/dispenser 76 which, except in the sense that it is designed to handle another modified form of ligator six-pack, such as those shown at 78, 80, 82, 84, has features like those found in the previously described charger/dispensers.

The particular ligator six-packs illustrated here includes somewhat circular central sprues, such as sprue 84*a*, each of which includes an elongate rectilinear central opening, such as central opening 84*b*, which is like previously mentioned opening 74*a*. Upwardly extending rectilinear posts, such as post 76*a*, extend frictionally into such openings to furnish principal gripping and retention of the ligator six-packs.

Fan-shaped groupings of hemostat-guide recesses, such as the grouping shown generally at 76b, and with an associated ligator six-pack in place on the charger/dispenser, operate in the manners described above for the recesses formed in the other two-described embodiments of charger/dispensers to guide the beaks in the jaw of a hemostat into a position for precisely gripping, plucking and removing an O-ring ligator from a six-pack, without appreciably occluding that ligator's central opening.

Turning attention briefly to FIG. 13, here there is illustrated a further modified form of the invention including slightly differing which can be imagined as being located at the upper right ends of either charger/ dispenser 66 as pictured in FIG. 9 or charger/dispenser 76 as pictured in FIG. 11. In this modification, instead of there being, as a plucking element, a two-tined fork, what is provided is an elongate projecting, preferably round-cross-section finger, such as finger 86, which is sized appropriately to be pressed into six-pack openings such as those shown in FIGS. 9 and 11, respectively, at 74a and 84b.

Thus, described herein are several different modifications of charger/dispensers which are constructed in accordance with the important features set forth above relating to the present invention. The operations and uses of each of these embodiments can be readily understood from the operational description given in conjunction with charger/dispenser 20, and it can be seen that each of these embodiments offers all of the advantages ascribed to the invention.

One should recognize that, while ligator six-packs have been illustrated herein including O-ring ligators of a given size, which, in the case of a charger/dispenser like that pictured in FIG. 1, have their tires slightly compressed when held in place, other ligator sizes including ones containing much smaller O-rings can also be handled according the invention. In relation to handling such other size ligator units, or for that matter other kinds of ligator units, it is simply required, inter alia, that the designed charger/dispenser include surface structure which frictionally and principally grips the sprue-portion, for example, of the ligator pack, and includes canal structure which effectively guides the beaks in the jaw of a hemostat appropriately to grip an about-to-be-removed ligator element as is discussed above.

Accordingly, while a preferred embodiment of the invention and several modifications thereof have been described and illustrated herein, it is appreciated that other variations and modifications may be employed without departing from the spirit of the invention.

It is claimed and desired to secure by Letters Patent:

1. A charger/dispenser for orthodontic O-ring ligator carrier structure of the type including a carrier having plural hemostat-jaw-separable, open-center, generally planar, annular O-ring ligators with annular faces, said ligators being removably joined to such a carrier, said charger/dispenser comprising:

a ligator structure including an integrally molded ligator-carrier having removably joined thereto plural generally planar, annular O-ring ligators having annular faces, said ligator structure further including first generally vertical side-wall features, and a dispenser chargeable with plural ones of said ligator structures, said dispenser including a body;

retaining structure formed in said body for retaining, frictionally and releasably, one or more of said ligator structures in a condition with said plural ligators in said ligator structure having their annular faces substantially fully exposed, said retaining structure including second opposed generally vertical side-wall surface features dimensioned for frictional, interference fit with said first generally vertical side-wall features of the ligator structure thereby releasably to position and orient the ligator structure on said body; and plural hemostat-jaw guide structures formed in said body adjacent said retaining structure, said guide structures corresponding with the plural ligators and each including third opposed, inwardly tapered side-walls joined to one another at a convergence thereof forming a canal dimensioned to receive therethrough a hemostat jaw in a manner whereby, with a ligator structure retained by said retaining structure, the plural ligators in the ligator structure are positioned adjacent a corresponding one of said guide structures, with each of said guide structures, under such circumstances, being effective to guide one of the two gripping beaks in the jaw of a hemostat through said canal and between said opposed side walls into a limit-defined ligator-removing position relative to such a ligator wherein the jaw can fully grip the ligator without occluding the open center therein.

2. The charger/dispenser of claim 1, wherein said retaining structure includes a recess having side-walls formed in the surface of said body adjacent said guide structures, said recess substantially conforming, at least to a portion of the shape of the ligator structure in a manner whereby, with the ligator structure within said recess, the side-walls of the recess frictionally contact the ligator structure for releasable retention thereof.

3. The charger/dispenser of claim 1 which is for use in conjunction with a ligator structure which further includes an elastically deformable opening in the carrier providing the second corresponding opposed side-wall surface features of the ligature structure, and wherein said retaining structure includes a post providing said first opposed side-wall surface features of said retaining structure projecting from the surface of said body for receiving such a ligator structure frictionally in a manner whereby the post extends through such an opening.

4. The charger/dispenser of claim 1, wherein said body has a ligator-structure supporting surface that forms a part of said recess formed within said body and wherein said canal of said hemostat-jaw guide structure opens to said supporting surface and is defined by sidewalls that terminate at a limit-defining back-wall which defines an ingression limit into said canal for the beak of a hemostat.

5. The charger/dispenser of claim 4, wherein the sidewalls of the canal, progressing therein toward said backwall, converge to define a deep center for the backwall and operate to direct the elongate incoming beak of a hemostat toward that center so that the longitudinal axis of that beak is disposed substantially parallel to the plane of a ligator associated with the canal, and substantially normal to a line tangent to such a ligator adjacent the portion thereof exposed by the canal.

6. The charger/dispenser of claim 4, wherein with respect to the usual gripping plane of said canal is further defined by a floor adjacent said sidewalls and said backwall in a manner whereby said floor is effective to support the beak of a hemostat jaw when such beak is in the mentioned ingression limit-defined condition, so that the gripping plane of the jaw is substantially coextensive with the plane of a ligator associated with the canal.

7. The charger/dispenser of claim 4, wherein said limit-defining backwall is located in a manner that prevents the beaks in the jaw of a hemostat from occluding the open center of a ligator.

8. The charger/dispenser of claim 1 which further comprises a plucking element joined to said body for plucking a loose individual ligator structure which is free of the charger/dispenser.

9. The charger/dispenser of claim 1 which further includes, within said body, a ligator-structure ejection passage adjacent said friction retaining structure, said ejection passage permitting the ligator structure to be ejected from releasable capture within said recess of said body.

10. A charger/dispenser for plural carriers of plural ones of O-ring ligators each being removably joined to the carrier, said charger/dispenser comprising:

a body, and retaining structure formed in said body for releasably simultaneously retaining the plural carriers in an array of defined positions and orientations such that one or more of the plural carriers of plural ones of the O-ring ligators may be loaded onto said body thereby to charge said charger/dispenser with the plural carriers being releasably retained by said retaining structure thereby to facilitate dispensing from said charger/dispenser the O-ring ligators one at a time from a selected one of the plural ones of the releasably retained carriers, said retaining structure including structural surface features formed therein and configured for frictional engagement with each of the plural carriers for releasable retention of each of the plural carriers within said retaining structure for loading of each of the plural carriers onto said body.

11. The charger/dispenser of claim 10 for plural configuration-differentiated carriers, wherein said retaining structure is configured for releasably retaining the plural configuration-differentiated carriers.

12. The charger/dispenser of claim 11 which further comprises at least two carriers that are color-differentiated from one another.

13. The charger/dispenser of claim 10 which further comprises at least two carriers the O-ring ligators of a first of which are size-differentiated from the O-ring ligators of the other.

14. The charger/dispenser of claim 10 wherein said releasable retaining structure includes structural surface features configured for frictional engagement with each of the plural carriers.

15. The charger/dispenser of claim 10 which further comprises a plucking element joined to said body for plucking a loose individual ligator structure which is free of the charger/dispenser.

16. The charger/dispenser of claim 10 which further includes, within said body, a ligator-structure ejection passage adjacent said friction retaining structure, said ejection passage permitting the ligator structure to be ejected from releasable capture within said recess of said body.

* * * * *